(12) United States Patent
Schumacher et al.

(10) Patent No.: US 9,816,908 B2
(45) Date of Patent: Nov. 14, 2017

(54) LIQUID DENSITY MEASURING DEVICE

(71) Applicants: James Joseph Schumacher, Kaukauna, WI (US); Angela Kristine Murphy Schumacher, Kaukauna, WI (US)

(72) Inventors: James Joseph Schumacher, Kaukauna, WI (US); Angela Kristine Murphy Schumacher, Kaukauna, WI (US)

( * ) Notice: Subject to any disclaimer, the term of this patent is extended or adjusted under 35 U.S.C. 154(b) by 115 days.

(21) Appl. No.: 14/934,714

(22) Filed: Nov. 6, 2015

(65) Prior Publication Data

US 2017/0131195 A1  May 11, 2017

Related U.S. Application Data

(60) Provisional application No. 62/076,268, filed on Nov. 6, 2014, provisional application No. 62/146,664, filed on Apr. 13, 2015.

(51) Int. Cl.
*G01N 9/00* (2006.01)
*G01N 9/18* (2006.01)

(52) U.S. Cl.
CPC .................................... *G01N 9/18* (2013.01)

(58) Field of Classification Search
CPC .............. G01N 9/10; G01N 9/12; G01N 9/18
USPC ................................... 73/444, 448, 449, 451
See application file for complete search history.

(56) References Cited

U.S. PATENT DOCUMENTS

| | | | | | |
|---|---|---|---|---|---|
| 576,537 | A | * | 2/1897 | Barry ....................... | G01N 9/12 374/141 |
| 1,831,315 | A | * | 11/1931 | Myers ....................... | G01N 9/12 73/449 |
| 2,809,525 | A | * | 10/1957 | Savage .................... | G01N 9/12 374/156 |

* cited by examiner

*Primary Examiner* — Benjamin Schmitt
(74) *Attorney, Agent, or Firm* — Smith Keane LLP

(57) ABSTRACT

A liquid density measuring device for use with a hydrometer comprising a vessel for receiving a liquid sample with a temperature calibration gauge having a thermo sensing end in contact with the liquid sample within the vessel. The gauge including a readout can be either analog or digital. The readout indicates a number relative to a current temperature of the liquid sample as sensed by the gauge. The number indicated on the readout being a desired hydrometer reading at the current temperature of the liquid sample. The readout will change to indicate a different desired hydrometer reading if the liquid sample changes temperature.

2 Claims, 9 Drawing Sheets

FIG. 5

| °F | BRIX Scale Reading | °F | BRIX Scale Reading | °F | BRIX Scale Reading | °F | BRIX Scale Reading |
|---|---|---|---|---|---|---|---|
| 32 | 68.3 | 82 | 65.7 | 132 | 63.1 | 182 | 60.4 |
| 33 | 68.2 | 83 | 65.6 | 133 | 63.0 | 183 | 60.4 |
| 34 | 68.2 | 84 | 65.6 | 134 | 62.9 | 184 | 60.3 |
| | | 85 | 65.5 | 135 | 62.9 | 185 | 60.3 |
| 36 | 68.1 | 86 | 65.5 | 136 | 62.8 | 186 | 60.2 |
| 37 | 68.0 | 87 | 65.4 | 137 | 62.8 | 187 | 60.2 |
| 38 | 68.0 | 88 | 65.4 | 138 | 62.7 | 188 | 60.1 |
| 39 | 67.9 | 89 | 65.3 | 139 | 62.7 | 189 | 60.0 |
| 40 | 67.9 | 90 | 65.3 | 140 | 62.6 | 190 | 60.0 |
| 41 | 67.8 | 91 | 65.2 | 141 | 62.6 | 191 | 59.9 |
| 42 | 67.8 | 92 | 65.2 | 142 | 62.5 | 192 | 59.9 |
| 43 | 67.7 | 93 | 65.1 | 143 | 62.5 | 193 | 59.8 |
| 44 | 67.7 | 94 | 65.1 | 144 | 62.4 | 194 | 59.8 |
| 45 | 67.6 | 95 | 65.0 | 145 | 62.4 | 195 | 59.7 |
| 46 | 67.6 | 96 | 64.9 | 146 | 62.3 | 196 | 59.7 |
| 47 | 67.5 | 97 | 64.9 | 147 | 62.3 | 197 | 59.6 |
| 48 | 67.5 | 98 | 64.8 | 148 | 62.2 | 198 | 59.6 |
| 49 | 67.4 | 99 | 64.8 | 149 | 62.2 | 199 | 59.5 |
| 50 | 67.4 | 100 | 64.7 | 150 | 62.1 | 200 | 59.5 |
| 51 | 67.3 | 101 | 64.7 | 151 | 62.1 | 201 | 59.4 |
| 52 | 67.3 | 102 | 64.6 | 152 | 62.0 | 202 | 59.4 |
| 53 | 67.2 | 103 | 64.6 | 153 | 61.9 | 203 | 59.3 |
| 54 | 67.2 | 104 | 64.5 | 154 | 61.9 | 204 | 59.3 |
| 55 | 67.1 | 105 | 64.5 | 155 | 61.8 | 205 | 59.2 |
| 56 | 67.1 | 106 | 64.4 | 156 | 61.8 | 206 | 59.2 |
| 57 | 67.0 | 107 | 64.4 | 157 | 61.7 | 207 | 59.1 |
| 58 | 67.0 | 108 | 64.3 | 158 | 61.7 | 208 | 59.0 |
| 59 | 66.9 | 109 | 64.3 | 159 | 61.6 | 209 | 59.0 |
| | | 110 | 64.2 | 160 | 61.6 | 210 | 58.9 |
| 61 | 66.8 | 111 | 64.2 | 161 | 61.5 | | |
| 62 | 66.7 | 112 | 64.1 | 162 | 61.5 | 212 | 58.8 |
| 63 | 66.7 | 113 | 64.1 | 163 | 61.4 | 213 | 58.8 |
| 64 | 66.6 | 114 | 64.0 | 164 | 61.4 | 214 | 58.7 |
| 65 | 66.6 | 115 | 63.9 | 165 | 61.3 | 215 | 58.7 |
| 66 | 66.5 | 116 | 63.9 | 166 | 61.3 | 216 | 58.6 |
| 67 | 66.5 | 117 | 63.8 | 167 | 61.2 | 217 | 58.6 |
| 68 | 66.4 | 118 | 63.8 | 168 | 61.2 | 218 | 58.5 |
| 69 | 66.4 | 119 | 63.7 | 169 | 61.1 | 219 | 58.5 |
| 70 | 66.3 | 120 | 63.7 | 170 | 61.0 | 220 | 58.4 |
| 71 | 66.3 | 121 | 63.6 | 171 | 61.0 | 221 | 58.4 |
| 72 | 66.2 | 122 | 63.6 | 172 | 60.9 | 222 | 58.3 |
| 73 | 66.2 | 123 | 63.5 | 173 | 60.9 | 223 | 58.3 |
| 74 | 66.1 | 124 | 63.5 | 174 | 60.8 | 224 | 58.2 |
| 75 | 66.1 | 125 | 63.4 | 175 | 60.8 | 225 | 58.2 |
| 76 | 66.0 | 126 | 63.4 | 176 | 60.7 | 226 | 58.1 |
| 77 | 66.0 | 127 | 63.3 | 177 | 60.7 | 227 | 58.1 |
| 78 | 65.9 | 128 | 63.3 | 178 | 60.6 | 228 | 58.0 |
| 79 | 65.8 | 129 | 63.2 | 179 | 60.6 | 229 | 58.0 |
| 80 | 65.8 | 130 | 63.2 | 180 | 60.5 | 230 | 57.9 |
| 81 | 65.7 | 131 | 63.1 | 181 | 60.5 | 231 | 57.9 |

FIG. 6 (PRIOR ART)

FRAGILE
Never drop the hydrometer into your testing cup.

Hot Test ⟶

Cold Test ⟶

"Brix" is a measurement used to calculate sugar density. Maple syrup is no less than 66% sugar.

The "Baumé" scale is used to measure the density of various liquids in comparison to the density distilled water which is 0.

Smoky Lake Maple Products offers of full line of high quality maple equipment.

(920) 202-4500
208 N 12th St. Hilbert, WI 54129
SmokyLakeMaple.com

HOW TO USE A
Maple Syrup Hydrometer

HOT TEST

1. Fill a testing cup at least 8" deep with hot, boiling maple syrup. IMPORTANT: Draw syrup directly from your boiling pans. Do NOT allow the syrup to cool. Syrup should be 211°F for best accuracy. CAUTION: Syrup will be hot. Wear protective clothing.
2. Slowly lower the clean hydrometer bulb-side-down *all the way* into the testing cup. IMPORTANT: A hydrometer is a fragile instrument. Never *drop* the hydrometer into the testing cup. It could crash into the bottom of the cup and break.
3. Allow the hydrometer to float and observe top red band which is labeled "Hot Test".
   - **If the band is *level*** to the surface of the syrup, it is perfect density and you are done boiling.
   - **If the band is *below*** the surface, continue boiling.
   - **If the band is *above*** the surface of the syrup, you have boiled it too far. In that case, slowly add hot sap to the syrup to thin it out and then repeat steps 1–3.

COLD TEST

This test is just like the hot test, except you will use room temperature maple syrup (60°F) and you will measure using the bottom red band of the hydrometer which is labeled "Cold Test".

TIPS FOR ACCURACY

Keep your hydrometer clean.

Allow the hydrometer to stabilize before making a reading.

Note that a maple *syrup* hydrometer is *not* intended for measuring raw maple sap. You will need a sap hydrometer or refractometer for that purpose.

Make sure the paper inside the hydrometer is not loose. In the rare event that the paper becomes loose, we will send you a replacement.

COMPENSATION CHART

| Syrup Temp F° | Brix Adjustment |
|---|---|
| 209 | +8 |
| 193 | +7 |
| 176 | +6 |
| 158 | +5 |
| 140 | +4 |
| 120 | +3 |
| 100 | +2 |
| 80 | +1 |
| 60 | 0 |
| 40 | -1 |

EXAMPLE: If the hydrometer floats at 65.6°Brix in syrup whose temperature is 80°F, add 1.0° Brix to the hydrometer reading to calculate the actual sugar content. 65.6 + 1 = 66.6°Brix

LIQUID DENSITY MEASURING DEVICE

CROSS-REFERENCE TO RELATED APPLICATION

The present application claims priority to earlier filed U.S. Provisional Application Ser. No. 62/076,268, filed on Nov. 6, 2014, and Ser. No. 62/146,664, filed on Apr. 13, 2015, the disclosures of which are included herein in their entirety.

BACKGROUND

In many industries, it is desirable to be able to continually test and measure the density of a liquid being processed to determine what stage the liquid is at. A hydrometer is often used to measure the specific gravity or relative density of the liquid being processed. To use such a hydrometer, a sample of liquid may be drawn into a testing cup. The hydrometer may then be placed into the cup and the level at which the hydrometer floats within the sample is recorded from a graduated scale on the hydrometer. The raw reading of this sort of measuring device can be affected by temperature. If the liquid being tested is warmer, the liquid may be less viscous, even if it has the same amount of material suspended in the same volume of water. So, at different temperatures, the hydrometer reading for the same density may differ. These differences in reading based on temperature are usually compensated for by reference to a table showing, for a given density, a list of values that should be read at different temperatures.

By way of a non-limiting example, in the maple syrup industry, it desirable to test the sugar content of the sap as it is being processed to determine progress. As the sugar concentration increases (as the sap is reduced), the temperature of boiling or vaporization increases. Thus, as the sap being processed gets closer to the desired concentration of sugar, the value to be read from the hydrometer differs from when the sap is first introduced into the process. Conventional approaches to determining the density (and sugar concentration) of the sap being processed into syrup recommend sampling the liquid at as close to the same temperature as possible each time. Standard hydrometers used in the industry are calibrated for use at a set temperature, typically either reading in the BRIX scale and/or the Baume scale. When readings are taken at a different temperature from the set temperature, the user consults a table to determine the reading that should be read from the hydrometer to achieve the BRIX or Baume reading for the desired sugar concentration. This conventional process is shown in FIG. 6.

Other industries, such as but not limited to the brewing and the distilling industries, also use hydrometers to measure density or concentrations at different points in the brewing and/or distilling process. These industries also deal with temperature ranges that can affect the readings taken directly from the hydrometer and which are corrected to a proper baseline through the use of conversion tables.

Improvements to these conventional approaches to measuring the density or specific gravity of a liquid to determine concentration of elements within the liquid are desirable.

BRIEF DESCRIPTION OF THE DRAWINGS

The accompanying drawing figures, which are incorporated in and constitute a part of the description, illustrate several aspects of the present disclosure and together with the description, serve to explain the principles of the present disclosure. A brief description of the figures is as follows:

FIG. 5 is a table for use with a sample hydrometer, showing the reading that a user should read on a hydrometer for a reduced maple sap liquid that has reached the desired concentration of sugar at a range of temperatures, illustrated in BRIX units, with different values highlighted that correspond to reading for desired density at particular temperatures.

FIG. 6 is an instruction page describing a conventional prior art approach to the use of a hydrometer to determine if a reduced maple sap liquid has adequate sugar concentration to become syrup, with a more generalized version of the table of FIG. 5, also illustrated in BRIX units.

DETAILED DESCRIPTION

Reference will now be made in detail to exemplary aspects of the present disclosure which are illustrated in the accompanying drawings. Wherever possible, the same reference numbers will be used throughout the drawings to refer to the same or like parts.

Figure 1:
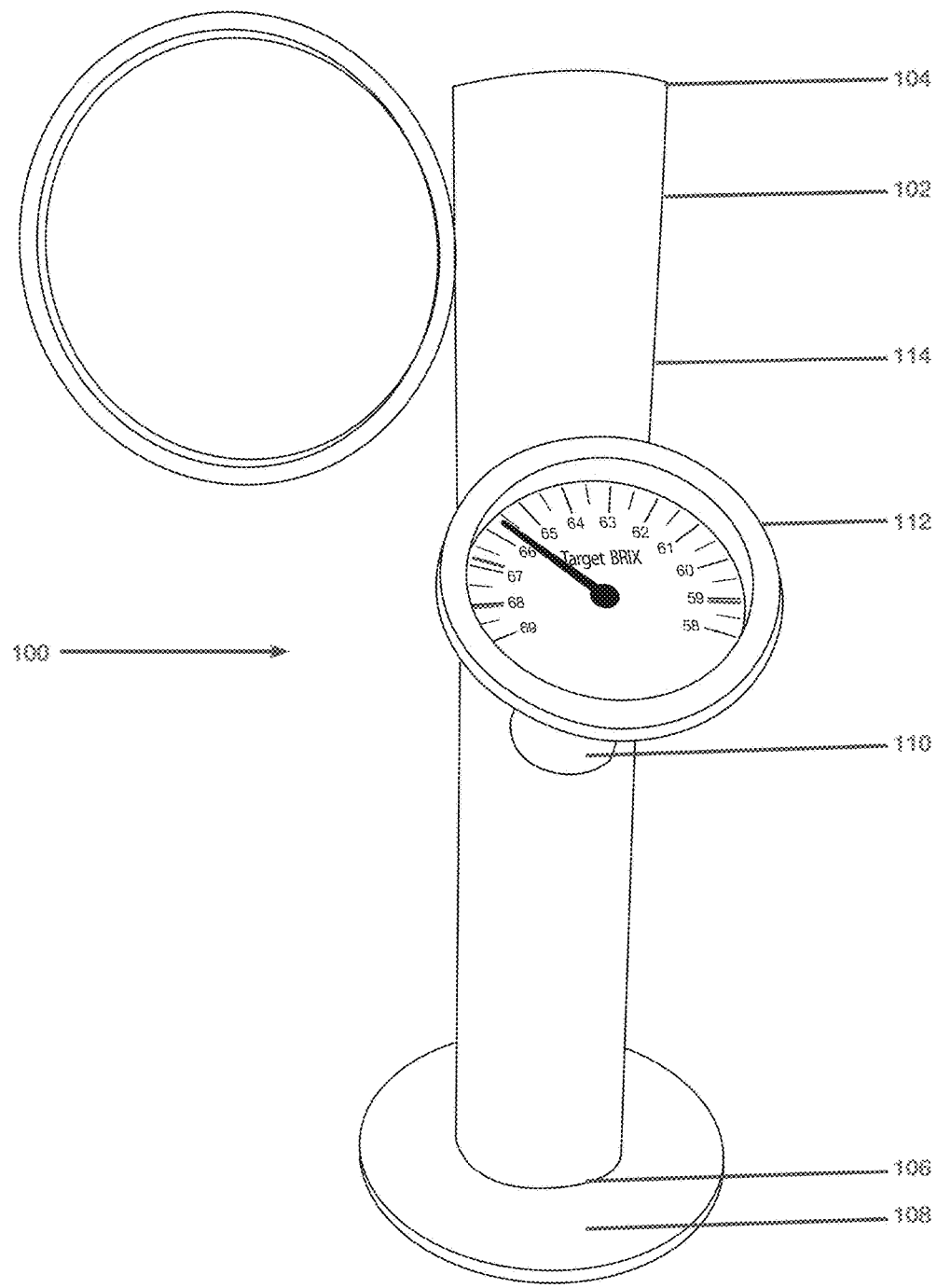
FIG. 1 is a first image of a liquid density measuring device according to the present disclosure.
Figure 2:
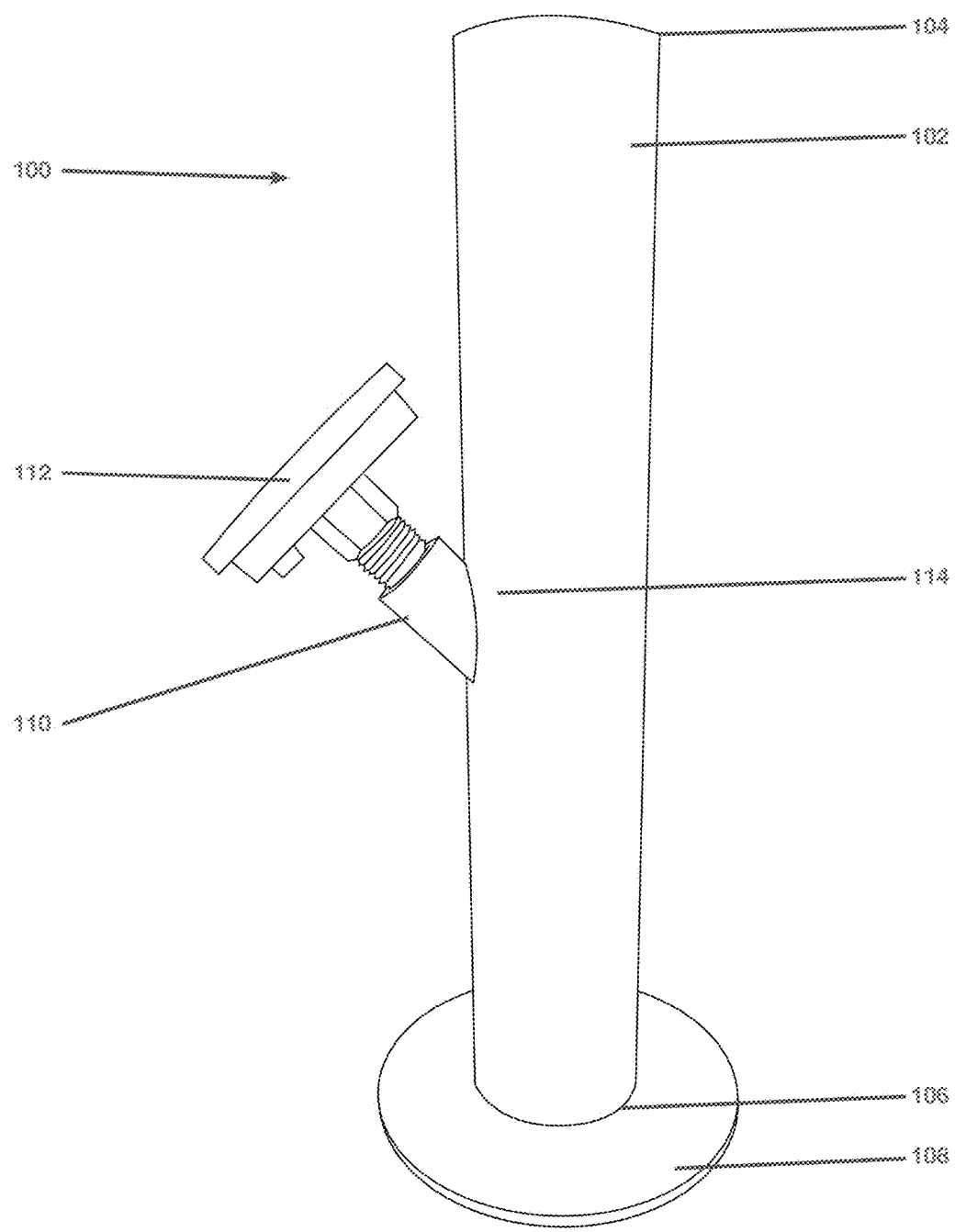
FIG. 2 is a second image of the liquid density measuring device of FIG. 1.

Referring now to FIGS. 1 and 2, a liquid density measuring device 100 according to the present disclosure may include a liquid receiving vessel or cup 102 with an open top 104 and a closed base 106. Base 106 may also include a larger diameter disk 108 or other structure to assist in stabilizing the device when it is in use. Positioned between top 104 and base 106 may be a mounting bung or tap 110 into which a temperature calibration gauge 112 may be removably mounted. Tap 110 should include an opening through an outer wall 114 of device 100 permitting gauge 112 to be in fluid communication with any liquid within cup 102. A handle 116 may also be included as part of device 100 to improve ease of handling, particularly when hot liquids may be tested using device 100.

Figure 3:
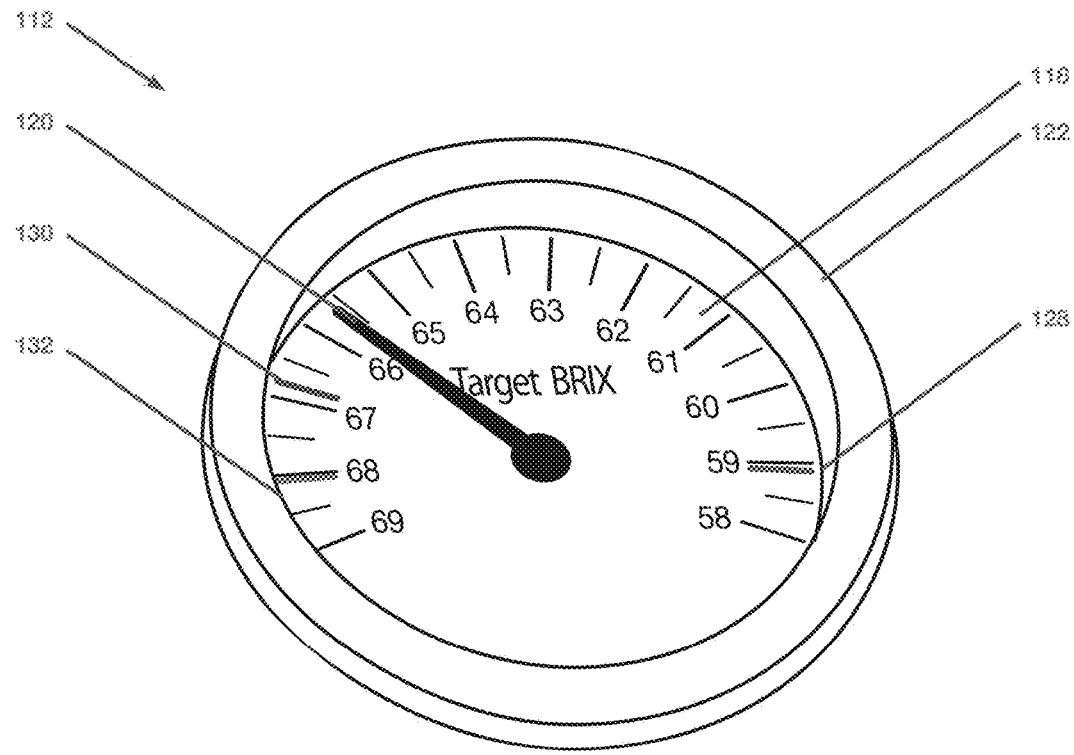
FIG. 3 is a closer image of a dial of a temperature calibration gauge of the liquid measuring device of FIG. 1.
Figure 4:
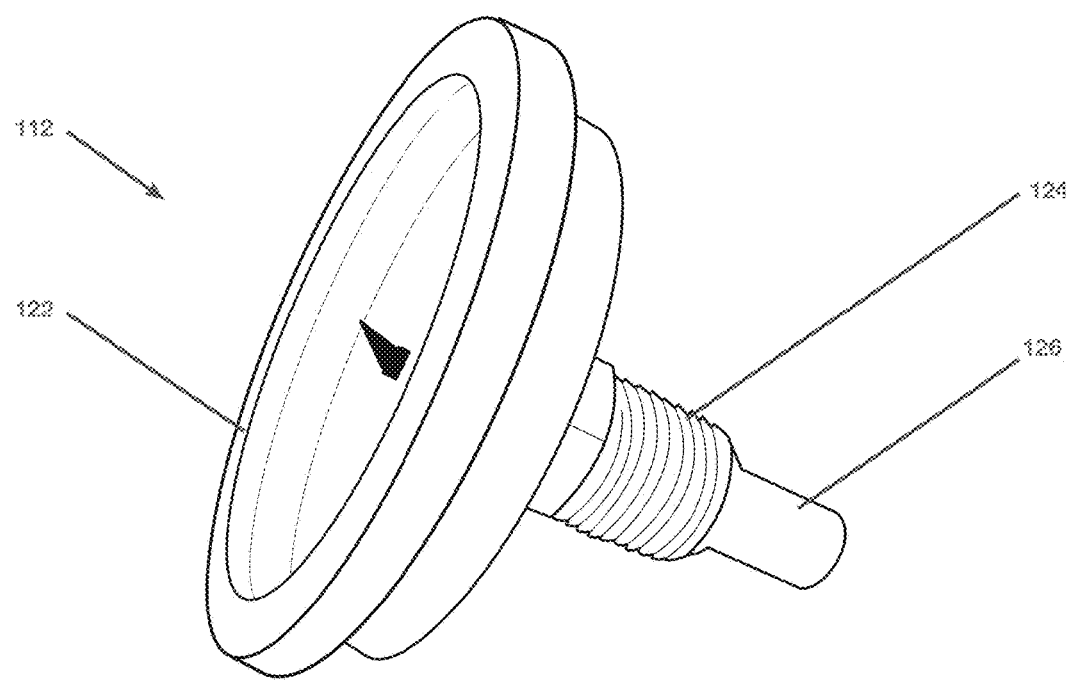
FIG. 4 is a perspective image of the temperature calibration gauge of FIG. 3.

Referring to FIGS. 3 and 4, temperature calibration gauge 112 may include a calibrated dial 118 with a needle 120 that moves about the dial in response to the temperature of the liquid being tested within device 100. Dial 118 and needle 120 may be contained within a housing 122. Housing 122 may include a threaded portion 124 extending opposite dial 120 and which is sized and configured to be threadably received within tap 110. Extending beyond threaded portion 124 may be a thermo sensing portion 126 that would be in fluid communication with any fluid within cup 102 of device 100 when gauge 112 is received within tap 110. While gauge 112 is shown as being configured to be threadably received within tap 110, it is not intended to limit the nature of the connection between the gauge and the cup or tap. While not preferable, it is anticipated that gauge 112 may be permanently mounted to cup 102. It is further anticipated that other removable mounting arrangements may be included, such as but not limited to a ¼ turn connection, a friction fit, or other similar and/or suitable connection options.

Figure 8:
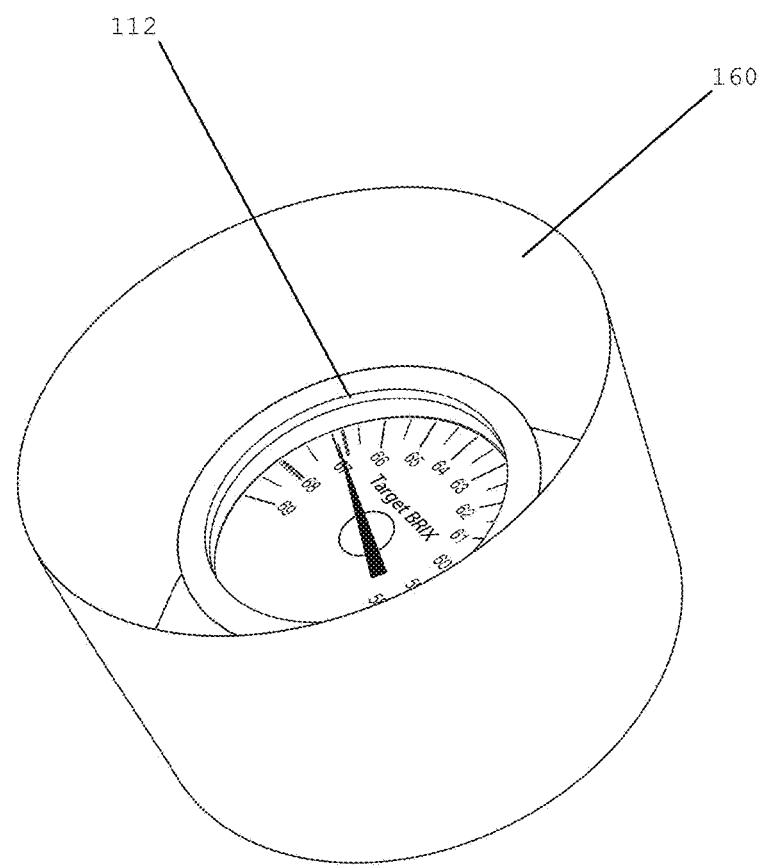
FIG. 8 is a perspective view of a floating temperature cup according to the present disclosure.
Figure 9:
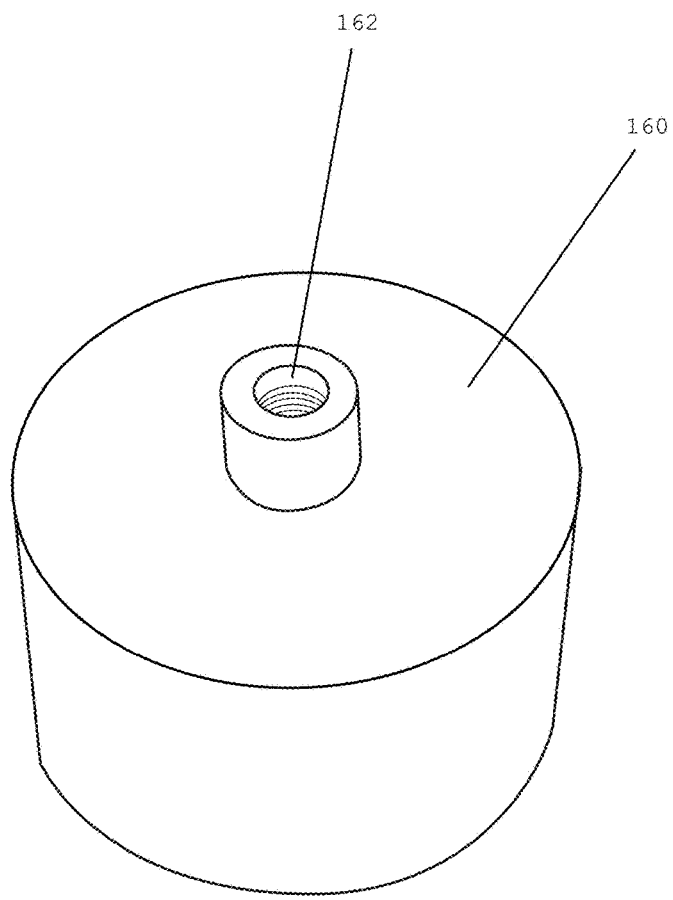
FIG. 9 is a second perspective view of the floating temperature cup of FIG. 8.

Alternatively, it may be desirable for a user to be able to determine if the density of a liquid is at a desired level without removing a sample from the vessel holding the liquid. If the liquid depth in its current vessel is sufficient, a floating temperature cup 160, illustrated in FIGS. 8 and 9 may be used to bring gauge 112 into fluid communication with the liquid while maintaining the dial above the surface of the liquid so the user can read the gauge. Floating cup 160 will preferably have a mounting opening 162 permitting gauge 112 to be mounted, as described above, so that thermos sensing portion 126 extends through floating cup 162 and into contact with any liquid the cup is floated on. Once the gauge shows the hydrometer reading of the corresponding to the current temperature and the desired density, the user may then place a hydrometer into the liquid adjacent the floating cup to see if the liquid is at the desired density.

Referring now to FIGS. 3 and 5, the function and operation of device 100 permits a user to place a reduced maple sap liquid sample whose specific gravity is to be tested into cup 102 and in contact with portion 126 of gauge 112. By letting the gauge sense the temperature of the liquid and the needle to move about dial 118 in response to the temperature sensed, the user can then read an adjusted value from dial 118. This adjusted value is the reading the hydrometer should produce when the liquid being tested is at the desired concentration. As shown, dial 118 is configured to indicate the reading from a hydrometer placed in the reduced maple sap liquid when the liquid has reached the desired percentage of sugar concentration. A most commonly used standard for a desired BRIX reading for a reduced maple sap liquid that is at the desired level of sugar concentration is 60. However, the reduced maple sap liquid sample would need to be at precisely 190 degrees when the reading is taken for this BRIX value to match the hydrometer reading.

If a liquid sample that is at exactly 190 degrees Fahrenheit were to be placed in cup 102 of device 100, needle 120 would indicate a reading of 60 BRIX on dial 120, which is the target reading for the hydrometer. For use in the maple syrup processing industry, this reading equates to 66.9% sugar within the reduced maple sap liquid being tested. At a standardized high temperature of 211 degrees Fahrenheit, the needle on the dial may indicate that the hydrometer should read 58.9 BRIX (marked on dial 112 with a first large dash 128) if the liquid is at the desired 66.9% sugar concentration. At a standardized low temperature of 60 degrees Fahrenheit, the needle on the dial may indicate that the hydrometer reading should be 66.9 BRIX (marked on dial 112 with a second large dash 130) for reduced maple sap liquid that is at the desired 66.9% sugar concentration. At any other temperature between these two extremes, the needle will indicate the correct hydrometer reading that should be observed for reduced maple sap liquid that is at the desired concentration of 66.9%. When a reading on the hydrometer shows a specific gravity below the desired level of concentration, the reduced maple sap liquid may continue to be heated and further reduced. When the reading on the hydrometer indicates a specific gravity that is at or higher than the desired level of concentration, then heating and reduction can be stopped and the liquid may be transferred for further processing and packaging. FIG. 6 illustrates a general procedure for the use of a hydrometer in the analysis of the sugar content of a reduced maple sap liquid and is provided as general information on the process used. The device of the present disclosure will render the steps of measuring the liquid at a precise temperature (either 211 degrees Fahrenheit or 60 degrees Fahrenheit corresponding to the red calibration marks on the hydrometer), or the determination of the desired correction to the BRIX reading corresponding to 66.9% sugar concentration unnecessary. The table shown in FIG. 6 is more generalized than the table in FIG. 5 but both represent the same adjusted hydrometer readings that should be read if the liquid tested is at the desired concentration.

As with any mechanical device, it is possible that the needle of gauge 112 may be pointing to an incorrect number at particular temperature. The mis-calibration may come about from a variety of reasons but needs to be addressed regardless of the cause. A zero calibration mark 132 (marked as a large dash 132 on dial 112), may be provided and positioned so that when portion 126 of gauge 112 is exposed to a liquid at 35 degrees Fahrenheit, the needle should be pointing at the calibration mark 132, located at 68.1. Gauge 112 will preferably be provided with an adjustment mechanism so that needle 118 may be moved left or right as needed until it points directly at mark 132. Since the remaining indications based on temperature are all relative, once the needle is adjusted to point at this zero mark, the remaining calibration should be correct as well.

Figure 7:
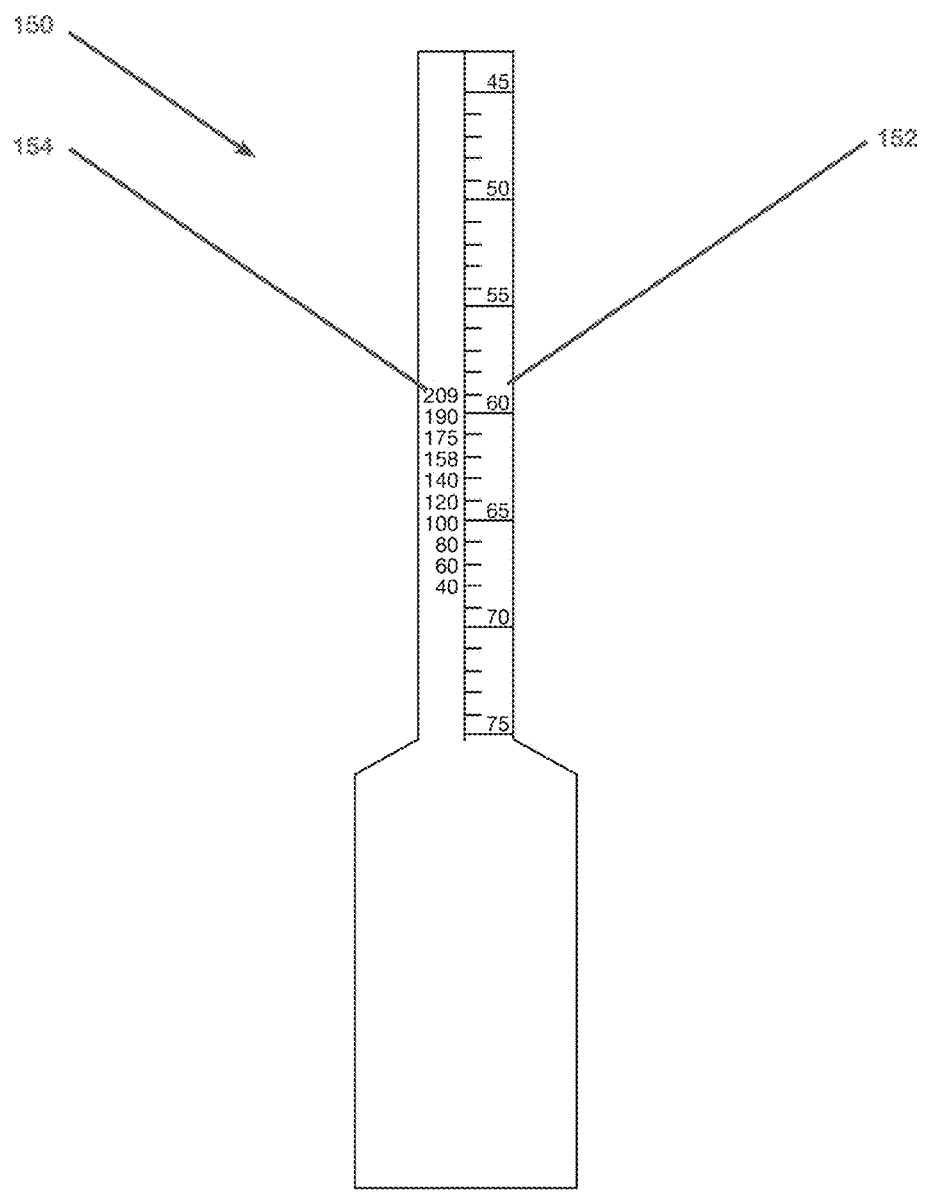
FIG. 7 illustrates a gauge insert for a hydrometer according to the present disclosure that incorporates a temperature correction marking for a desired concentration of a liquid.

An alternative embodiment of a temperature correction approach according to the present disclosure is illustrated in FIG. 7. A gauge insert 150 for positioning within a hydrometer may include a density scale 152, such as but not limited to the BRIX scale shown, and a temperature compensation scale 154, such as but not limited to the temperatures associated with or common to maple syrup processing. For this alternative embodiment to work, a liquid measuring device similar to device 100 might be used with a more traditional thermometer in place of the temperature calibration gauge. It is preferable that the thermometer and compensation scale 154 be listed in the same units for ease of use.

By way of a non-limiting example, a hydrometer configured with a gauge insert such as insert 150 may be used in conjunction with processing of maple sap into maple syrup. With gauge insert 150 positioned within a hydrometer, and properly calibrated, a person using the hydrometer would gather a sample of the processed sap to determine if it had reached the desired sugar concentration to be called syrup, within a liquid measuring device with a thermometer. The hydrometer with gauge insert 150 would then be placed in the sample cup so that the level of the liquid relative to the gauge insert may be visually inspected. The user would then consult the thermometer to see the temperature of the liquid within the cup. If the level of the liquid along the hydrometer relative to the compensation scale corresponds to the temperature of the liquid, then the liquid will have reached the desired density. If the liquid level corresponds to a higher number on the compensation scale, the liquid has not yet reached the desired density. Whereas conversely, if the level of the liquid corresponds to a lower number than the temperature, the liquid is too dense compared to the desired consistency.

Both embodiments of devices to measure liquid density according to the present disclosure represent approaches that will allow users to dispense with one or more of the separate elements that must be used to measure the density of a liquid in question. Most desirably, the user will no longer need to carry or consult a compensation chart or table such as shown in FIG. 6 after reading the temperature of the liquid. Integration of the temperature calibration gauge into the liquid cup itself combines several elements and further reduces the number of separate items that a user must access to measure liquid density. It is anticipated that other implementations of similar approaches that incorporate the compensation scale or table within the density measuring device may be obvious to a person of ordinary skill in the relevant technical field and it is not intended to limit the scope of the present disclosure to any one or more particular embodiments. By way of a non-limiting example, it is anticipated that device according to the present disclosure may include a digital readout that indicates a desired reading of a hydrometer for a given temperature instead of the analog dial arrangement illustrated in the attached drawings.

Many other industries have need for calibrated hydrometers that are read with an eye toward the temperature of the liquid to be able to precisely determine the concentration of, for example, sugar, alcohol, salt, etc., suspended within a liquid. The concentration of these compounds, suspended or dissolved within a water substrate, will determine the specific gravity of the liquid and thus determine the height that a hydrometer will float within the liquid. The device of the present application may be used in any number of industrial, workshop, facility or hobby settings where an accurate determination of the concentration of a liquid is to be measured. The device of the present disclosure will permit the user of such a device to measure the liquid at whatever temperature it might be at and still be able to quickly and accurately determine the desired reading on the hydrometer. No longer will such users have to carry and consult manual adjustment tables, such as shown in FIG. 6. Dial 120 of the gauge 112 may be configured as needed to indicate the correct value for whatever the desired reading of the hydrometer might be for whatever level of concentration and thus specific gravity is desired in the liquid being tested. The scale on the dial may be shown in BRIX, as in the illustrated example or may be adapted to other commonly used scales and ranges of hydrometer readings that may be used in other settings.

Several non-limiting examples of such other users for the device of the present disclosure may include: petroleum refiners, industrial chemical producers, pharmacological producers, fruit juice producers, wineries, distilleries, breweries, waste water treatment operations, analysis of automotive fluids and bleach and dye manufacturers. Several non-limiting examples of scales that may be used with the device of the present application may include: API Gravity, Baume, BRIX, Degrees Balling, Oechsle, Plato and Twaddle.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

What is claimed is:

1. A liquid density measuring device for use with a hydrometer, the liquid density measuring device comprising:
   a vessel for receiving a liquid sample;
   the vessel including a temperature calibration gauge with a thermo sensing end and permitting fluid communication between the liquid sample within the vessel and the thermo sensing end of the gauge;
   the temperature calibration gauge including a readout selected from one of a dial and a needle and a digital display; and,
   the readout configured to indicate a number relative to a current temperature of the liquid sample as sensed by the thermo sensing end of the temperature calibration gauge, the number indicated on the readout being a desired hydrometer reading for the liquid sample at the current temperature of the liquid sample;
   wherein the readout changes to indicate a different desired hydrometer reading if the liquid sample changes temperature.

2. A liquid density measuring device for use with a hydrometer, the liquid density measuring device comprising:
   a cup configured to receive a temperature calibration gauge with a thermo sensing end extending through the cup; wherein the cup is configured so that the cup and the temperature calibration gauge will float in a vessel containing a liquid whose density is to be checked with the thermo sensing end in fluid communication with the liquid when the cup and temperature calibration gauge are floating in the vessel;
   the temperature calibration gauge including a readout selected from one of a dial and a needle and a digital display; and,
   the readout configured to indicate a number relative to a current temperature of the liquid on which the cup and temperature calibration gauge are floating as sensed by the thermo sensing end of the temperature calibration gauge, the number indicated on the readout being a desired hydrometer reading for the liquid at the current temperature of the liquid;
   wherein the readout changes to indicate a different desired hydrometer reading if the liquid changes temperature.

* * * * *